United States Patent
Carpentier et al.

(10) Patent No.: US 7,241,849 B2
(45) Date of Patent: Jul. 10, 2007

(54) GROUP III BRIDGED METALLOCENE BASED ON CYCLOPENTADIENYL-FLUORENYL LIGANDS

(75) Inventors: Jean-François Carpentier, Acigne (FR); Evgueni Kirillov, Erlangen (DE); Abbas Razavi, Mons (BE)

(73) Assignee: Total Petrochemicals Research Feluy, Feluy (BE)

( * ) Notice: Subject to any disclaimer, the term of this patent is extended or adjusted under 35 U.S.C. 154(b) by 0 days.

(21) Appl. No.: 10/541,644

(22) PCT Filed: Jan. 6, 2004

(86) PCT No.: PCT/EP2004/000142

§ 371 (c)(1), (2), (4) Date: Dec. 16, 2005

(87) PCT Pub. No.: WO2004/060942

PCT Pub. Date: Jul. 22, 2004

(65) Prior Publication Data

US 2006/0116278 A1    Jun. 1, 2006

(30) Foreign Application Priority Data

Jan. 7, 2003   (FR) ................... 03 00086

(51) Int. Cl.
*C08F 4/52* (2006.01)
(52) U.S. Cl. .............. 526/164; 526/160; 526/170; 526/126; 526/943; 502/103; 556/53; 556/11; 556/12

(58) Field of Classification Search ............... 526/170, 526/160, 164, 943; 502/103, 164; 556/11, 556/12, 53
See application file for complete search history.

(56) References Cited

FOREIGN PATENT DOCUMENTS

WO    WO 00/56778 A1 * 9/2000

OTHER PUBLICATIONS

Qian et al. Organometallics, 2000, 19, 4134-4140.*
Lee et al. Organometallics, 1999, 18, 5124-5129.*
JP 7-258319 (abstract and translation in English).*

* cited by examiner

*Primary Examiner*—David W. Wu
*Assistant Examiner*—Rip A. Lee
(74) *Attorney, Agent, or Firm*—William D. Jackson; Tenley R. Krueger

(57) ABSTRACT

The present invention discloses a metallocene catalyst component of formula $(Flu-R''-Cp)M(\eta^3-C_3R'_5)(ether)_n$ (I) wherein Cp is a cyclopentadienyl, substituted or unsubstituted, Flu is a fluorenyl, substituted or unsubstitutted, R" is a structural bridge between Cp and Flu imparting stereorigidity to the component, M is a metal Group III of the Periodic Table, each R' is the same or different and is hydrogen or a hydrocarbyl having from 1 to 20 carbon atoms and n is 0, 1 or 2. It further discloses a process for preparing said catalyst component and its used in the controlled polymerisation of polar or non polar monomers.

20 Claims, 3 Drawing Sheets

GROUP III BRIDGED METALLOCENE BASED ON CYCLOPENTADIENYL-FLUORENYL LIGANDS

This invention relates to the field of metallocene catalyst systems based on a cyclopentadienyl-fluorenyl component containing a metal Group III of the Periodic Table. It also relates to controlled polymerisation based on such catalyst system.

In Razavi and Ferrara (A. Razavi, J. Ferrara, J. Organomet. Chem. 435, 299, 1992), it is shown that Group IV metallocenes of the formula

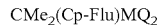

CMe$_2$(Cp-Flu)MQ$_2$ wherein M is a metal Group IVB of the Periodic Table, Cp-Flu is a cyclopentadienyl-fluorenyl ligand substituted or unsubstituted, CMe$_2$ is a bridge between the cyclopentadienyl and the fluorenyl and wherein Q is hydrocarbon having from 1 to 20 atoms or a halogen, are effective precursors for stereospecific and stereoselective polymerization of propylene. Upon activation with an alumoxane these compounds produce high molecular weight syndiotactic polypropylene with very high activities.

On the other hand, some lanthanide alkyl and hydride complexes stabilised by cyclopentadienyl moieties have been known for about two decades to act as single component catalysts able to polymerise α-olefins (ethyleneà and to initiate stereospecific polymerisation of polar monomers such as (meth)acrylates, but there is no systematic behaviour as some lanthanide complexes are active whereas others are completely unreactive. They are described for example in Ballard et al. (in D. G. H. Ballard, A. Courtis, J. Holton, J. McMeeking, R. Pearce, Chem. Commun. 1978, 994.), in Watson and Parshall (in P. L. Watson, G. W. Parshall, Acc. Chem. Res. 1985, 18, 51.), in Jeske et al. (in G. Jeske, H. Lauke, H. Mauermann, P. N. Swepston, H. Schumann, T. J. Marks, J. Am. Chem. Soc. 1985, 107, 809.), in Burger et al. (in B. J. Burger, M. E. Thompson, D. W. Cotter, J. E. Bercaw, J. Am. Chem. Soc. 1990, 112, 1566.) or in Yasuda (in H. Yasuda, Prog. Polym. Sci. 2000, 25, 573.).

Dash et al. (in A. K. Dash, A. Razavi, A. Mortreux, C. W. Lehmann, J.-F. Carpentier, Organometallics, 2002, 21, 3238.) have worked on the amine elimination reactions of homoleptic amides Ln[N (SiMe$_3$)$_2$]$_3$ wherein Ln is yttrium, lanthanum or neodymium with the isopropyledene-bridged CpH-CMe$_2$-FluH ligand. The resulting complex have been shown to be inactive in ethylene polymerization even upon activation with magnesium or aluminium alkyls.

Qian et al. (in C. Qian, W. Nie, J. Sun, J. Chem. Soc., Dalton Trans., 1999, 3283; and in C. Qian, W. Nie, J. Sun J. Organomet. Chem., 2001, 626, 171.) have shown that the salt metathesis reaction of LnCl$_3$(THF)$_n$ wherein Ln is Y or Lu, with the dilithiated species of the diphenyl-carbon-bridged Cp-CPh$_2$-Flu ligand gives the structurally characterized ionic complexes [(η$^5$,η$^5$-Cp-CPh$_2$-Flu)LnCl$_2$]$^-$[Li (THF)$_4$]$^+$ in good yields.

Another publication by the same group (C. Qian, W. Nie, Y. Chen and J. Sun, in J. Organomet. Chem. 645, 82, 2002.) discloses that the treatment of [(η$^5$,η$^5$-Cp-CPh$_2$-Flu)LuCl$_2$]$^-$ [Li(THF)$_4$]$^+$ with LiN(SiMe$_3$)$_2$ afforded, in a low yield of about 13%, the neutral complex (η$^5$,η$^5$-Cp-CPh$_2$-Flu)LuN (SiMe$_3$)$_2$, which was found to initiate polymerisation of caprolactone and methyl methacrylate (MMA); polymethyl methacrylate (PMMA) was produced in low activity at room temperature and contained about 60% rr dyads.

Other attempts by the same group (in C. Qian, W. Nie, Y. Chen, S. Jie, J. Organomet. Chem., 2002, 645, 82; and in W. Nie, C. Qian, Y. Chen, S. Jie, J. Organomet. Chem., 2002, 647, 114.) to extend this chemistry to "light" lanthanide metals such as for example La or Nd have failed; the successful syntheses of some derivatives [(Cp-CPh$_2$-Flu)Ln ((μ-H)$_3$BH)$_2$]$^-$[Li(THF)$_4$]$^+$ wherein Ln is La or Nd, also structurally characterised, stem from steric stabilisation of the system by versatile bridging bonding of tridentate BH$_4^-$ anions with lanthanide atom.

JP-A-07258319 discloses the preparation of the neutral carbyl complex {η$^5$,η$^5$-Cp-CMe$_2$-(2,7-tBu$_2$-Flu)}LnCH (SiMe$_3$)$_2$ via a two-step, one-pot procedure involving salt metathesis between YCl$_3$(THF), and Li$_2$[Cp-CMe$_2$-(2,7-tBu$_2$-Flu)], followed by subsequent transmetallation with LiCH(SiMe$_3$)$_2$. The title complex was characterised only by $^1$H NMR and claimed to initiate living polymerization of MMA at 0° C. to give a polymer with weight average molecular weight distribution M$_w$ of 512,000, a polydispersity index D of 1.66 and 78% rr dyads. The polydispersity index D is defined by the ratio M$_w$/M$_n$ of the weight average molecular weight to the number average molecular weight.

There is therefore no unified method to prepare in good yield bridged metallocene components based on cyclopentadienyl-fluorenyl ligands and on Group III metals and to prepare therefrom catalyst systems having good polymerisation capability.

In addition all known metallocene catalyst systems based on metals Group IV of the Periodic Table require costly and dangerous activating agents and are not suitable to polymerise polar monomers.

It is an aim of the present invention to prepare in good yield bridged metallocene components based on cyclopentadienyl-fluorenyl ligands and based on Group III metals.

It is another aim of the present invention to prepare catalyst components efficient in the controlled polymerisation of styrene.

It is a further aim of the present invention to prepare catalyst components capable of preparing syndiotactic polymethylmethacrylate.

More generally, the present invention aims at preparing catalyst systems efficient in the controlled polymerisation of polar or non polar monomers.

Accordingly, the present invention discloses a metallocene catalyst component of the general formula

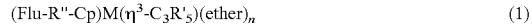

(Flu-R"-Cp)M(η$^3$-C$_3$R'$_5$)(ether)$_n$     (1)

wherein Cp is a cyclopentadienyl, substituted or unsubstituted, Flu is a fluorenyl, substituted or unsubstituted, M is a metal Group III of the Periodic Table, R" is a structural bridge between Cp and Flu (9-position) imparting stereorigidity to the component, each R' is the same or different and is hydrogen or an hydrocarbyl having from 1 to 20 carbon atoms and n is 0, 1 or 2.

The substituents on the cyclopentadienyl are not particularly limited, they can be the same or different and they include hydrocarbyls having from 1 to 20 carbon atoms.

The substituents on the fluorenyl are not particularly limited, they can be the same or different and they include hydrocarbyls having from 1 to 20 carbon atoms.

In the allyl group C$_3$R'$_5$, R' includes hydrogen or an hydrocarbyl having from 1 to 20 carbon atoms. It may also include a silyl group or a polybutadienyl chain.

The type of bridge present between the cyclopentadienyl and the fluorenyl in the above-described catalysts is not itself particularly limited. Typically R" comprises an alkylidene group having 1 to 20 carbon atoms, a germanium group (e.g. a dialkyl germanium group), a silicon group (e.g. a dialkyl silicon group), a siloxane group (e.g. a dialkyl siloxane group), an alkyl phosphine group or an amine group. Preferably, the substituent comprises a silyl radical or a hydrocarbyl radical having at least one carbon atom, to form the bridge, or a substituted or unsubstituted ethylenyl radical (e.g. —CH$_2$CH$_2$—). More preferably R" is isopropylidene (Me$_2$C), Ph$_2$C, ethylenyl, or Me$_2$Si, and most preferably R" is (Me$_2$C).

M is preferably yttrium, lanthanum or a member of the lanthanide series. Throughout this description, the term "lanthanide series" means the rare earth series of elements having atomic numbers of from 58 to 71. In the lanthanide series M is preferably neodymium, samarium. More preferably, M is yttrium.

The present invention also discloses a method for preparing the catalyst component (I) that comprises the steps of:
a) suspending MCl$_3$(THF)$_n$ in ether;
b) suspending a dilithium salt of (Cp-R"-Flu) in ether;
c) carrying out the salt metathesis reaction of suspensions a) and b) at a temperature of from −80° C. to 60° C., and wherein the molar ratio of suspensions b) to a) is less than 2;
d) crystallising the product obtained in c) from the ether;
e) retrieving a crystalline powder;
f) allylating the crystalline powder from step e) with ClMg(C$_3$R'$_5$) or Li C$_3$R'$_5$ or any equivalent allylating reagent in a solvent at a temperature of from −80° C. to 60° C., wherein R' is hydrogen or a hydrocarbyl having from 1 to 20 carbon atoms;
g) retrieving a neutral complex of formula

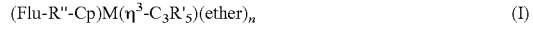
(Flu-R"-Cp)M(η$^3$-C$_3$R'$_5$)(ether)$_n$     (I)

The relative molar amounts of MCl$_3$(THF)$_n$ ligand and dilithium salt are preferably one to one.

The ether can be selected for example from tetrahydrofuran (THF), dioxane, diethyl oxide or diisopropyl oxide. Preferably, it is THF or diethyl oxide (Et$_2$O).

The solvent can be selected from an aliphatic or aromatic hydrocarbyl such as for example toluene, xylene, pentane, cyclohexane, heptane.

The crystalline powder obtained in step e) is extremely sensitive to air: it is not soluble in pentane, sparingly soluble in toluene and readily soluble in tetrahydrofuran (THF) or diethyl oxide.

X-ray diffraction studies of several suitable crystals isolated from the products of step e) and NMR studies suggested that two compounds are in equilibrium:
a compound of formula

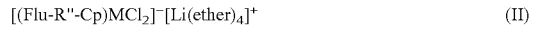
[(Flu-R"-Cp)MCl$_2$]$^-$[Li(ether)$_4$]$^+$     (II)

and
a compound of formula

[(Flu-R"-Cp)$_2$M]$^-$[Li(ether)$_4$]$^+$     (III)

That equilibrium is schematically represented in FIG. 1 that further discloses how the equilibrium is altered during allylation, and the $^1$H NMR spectra of the mixture of compounds (II) and (III) is represented in FIG. 2 as a function of temperature.

The anion of ionic formula (III) is represented in FIG. 3.

In another aspect, the present invention covers the use of metallocene component (I), with or without activating agent or transfer agent for the controlled polymerisation of polar or non polar monomers.

The present invention further discloses a process for homopolymerising polar or non polar monomers or for copolymerising polar or non polar monomers with a comonomer, said process comprising the steps of:
providing the metallocene component of formula (I);
optionally providing an activating agent or a transfer agent;
providing a monomer and an optional comonomer:
maintaining the system under polymerising conditions;
retrieving the desired polymer.

The optional activating agent includes Lewis acids having an ionising action and having a low or no co-ordinating capability. Typically, all the activators used with the metals Group IV of the Periodic Table can be used in the present invention. Suitable aluminium-containing activating agents comprise an alumoxane or an aluminium alkyl.

The alumoxanes that can be used in the present invention are well known and preferably comprise oligomeric linear and/or cyclic alkyl alumoxanes represented by the formula (I):

for oligomeric linear alumoxanes; and formula (II)

for oligomeric cyclic alumoxanes, wherein n is 1–40, preferably 10–20; m is 3–40, preferably 3–20; and R is a C$_1$–C$_8$ alkyl group, preferably methyl. Generally, in the preparation of alumoxanes from, for example, aluminium trimethyl and water, a mixture of linear and cyclic compounds is obtained.

Suitable boron-containing activating agents may comprise a triphenylcarbenium boronate, such as tetrakis-pentafluorophenyl-borato-triphenylcarbenium as described in EP-A-0427696:

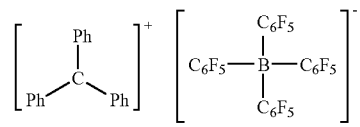

or those of the general formula below, as described in EP-A-0277004 (page 6, line 30 to page 7, line 7):

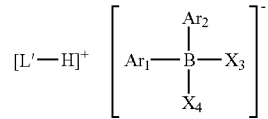

Other preferred activating agents include hydroxy isobutylaluminium and a metal aluminoxinate. These are particularly preferred when at least one Q in the general formula for metallocenes comprises an alkyl group.

Alkylating agents of the type $MgR'_2$ can also be used, wherein each R' is the same or different and is a hydrocarbyl having from 1 to 20 carbon atoms.

The transfer agents comprise for example H2 and hydrosilanes of the formula $HsiR'''_3$ wherein each R''' is the same or different and is either hudrogen or an hydrocarbyl having from 1 to 20 carbon atoms. It will be selected in accordance with the monomer to be polymerised.

The monomers that can be used in the present invention include non polar monomers such as for example ethylene, alpha-olefins, styrene and polar monomers such as for example acrylates or dienes. Preferably, styrene and methyl methacrylate have been used.

The catalyst system of the present invention may be employed in any type of homo- or co-polymerisation method, provided that the required catalytic activity is not impaired. In a preferred embodiment of the present invention, the catalyst system is employed in a bulk polymerisation process or in a solution polymerisation process, which is homogeneous, or in a slurry process, which is heterogeneous. In a solution process, typical solvents include THF or hydrocarbons having from 4 to 7 carbon atoms such as heptane, toluene or cyclohexane. In a slurry process, it is necessary to immobilise the catalyst system on an inert support, particularly a porous solid support such as talc, inorganic oxides and resinous support materials such as polyolefin. Preferably, the support material is an inorganic oxide in its finely divided form.

Suitable inorganic oxide materials that are desirably employed in accordance with this invention include group IIA, IIIA, IVA, or IVB metal oxides such as silica, alumina and mixtures thereof. Other inorganic oxides that may be employed, either alone or in combination with the silica or alumina, are magnesia, titania, zirconia, and the like. Other suitable support materials, however, can be employed, for example, finely divided functionalised polyolefins such as finely divided polyethylene.

Preferably, the support is a silica support having a surface area of from 200–700 $m^2/g$ and a pore volume of from 0.5–3 ml/g.

The polymerisation temperatures range from 20° C. up to 100° C.

The present invention also covers the polymers obtainable by polymerisation in the presence of the catalysts components described hereabove.

LIST OF FIGURES

EXAMPLES

Figure 1:
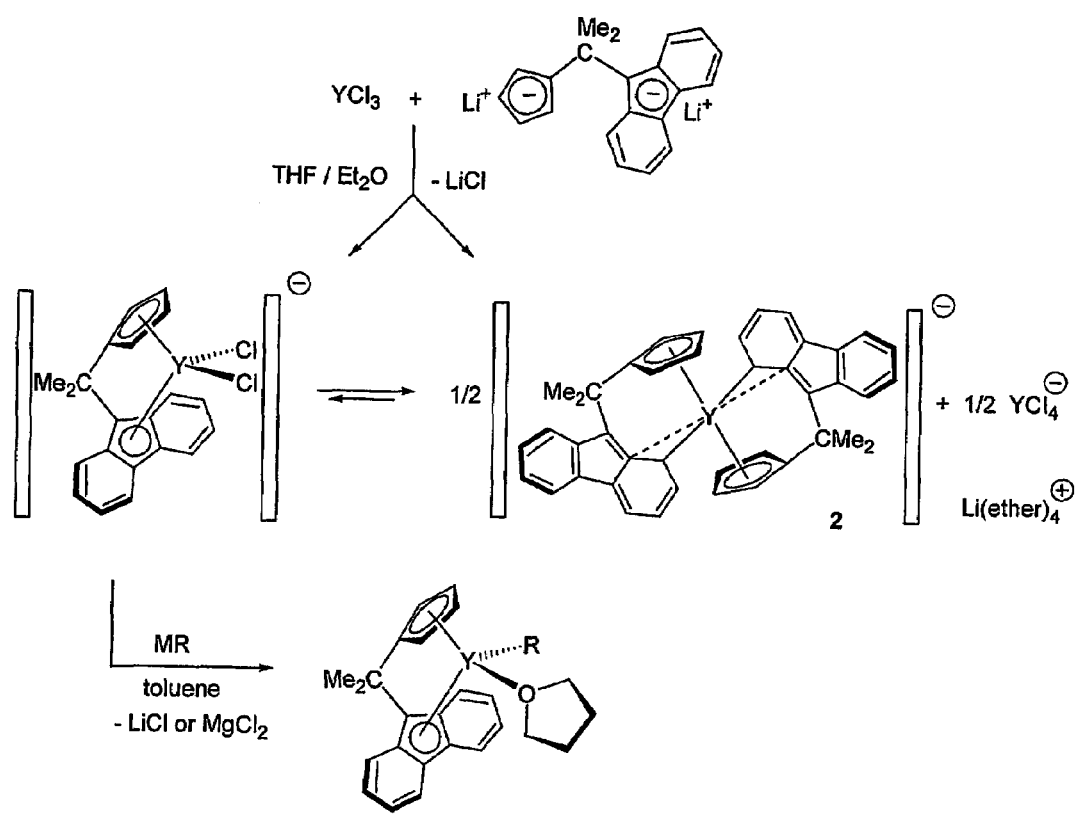
FIG. 1 represents the mechanism for the formation of compounds (I), (II) and (III). In this Figure, R represents $C_3R''_5$ as defined in the description.
Figure 2:
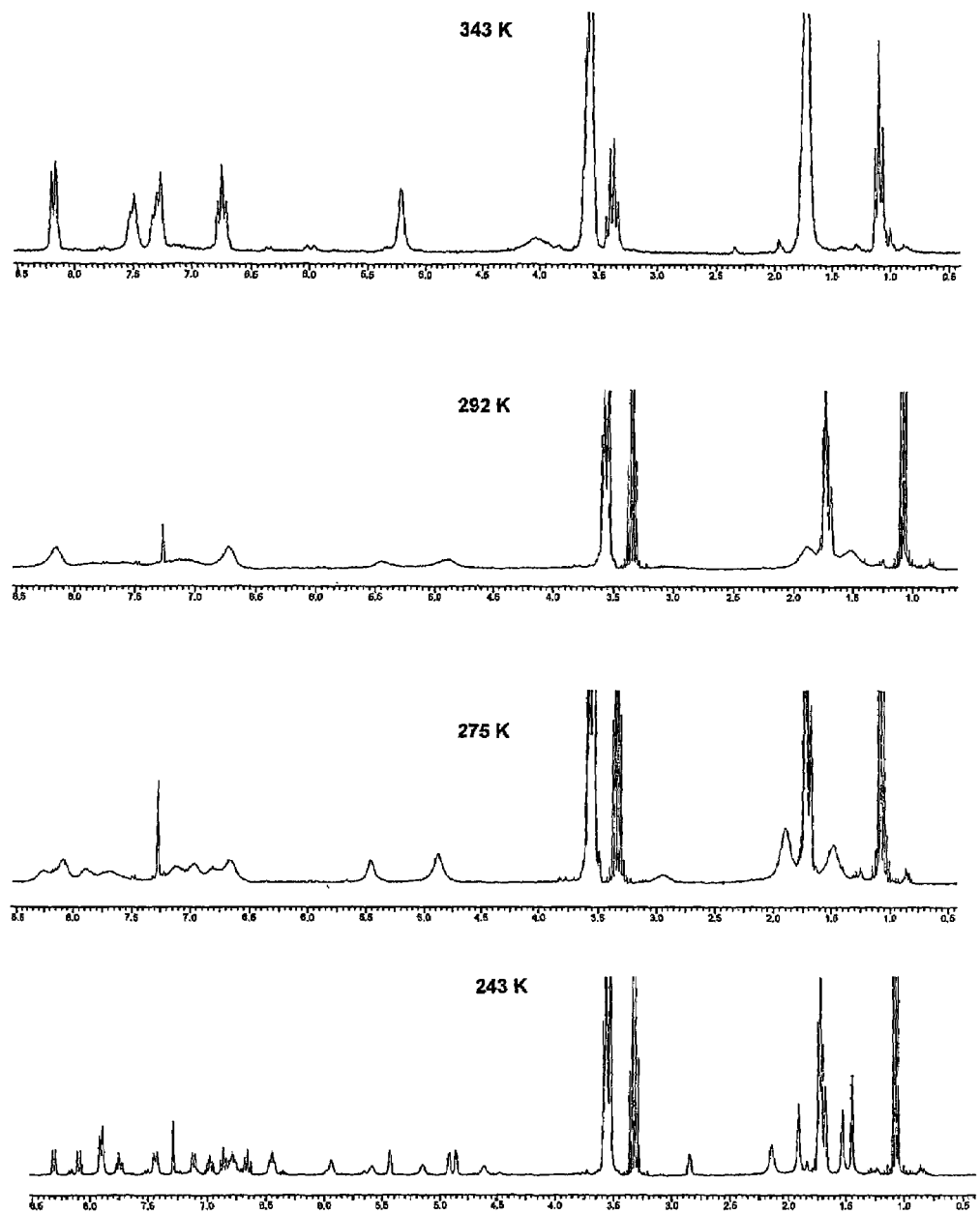
FIG. 2 represents a drawing of the crystal structure of the anion of $[(\eta^3,\eta^5\text{-Flu-}CR_2\text{-Cp})(\eta^1,\eta^5\text{-Flu-}CR\text{-Cp})Y]^-[Li(ether)_4]^+$. Ellipsoids correspond to 50% probability.
Figure 3:
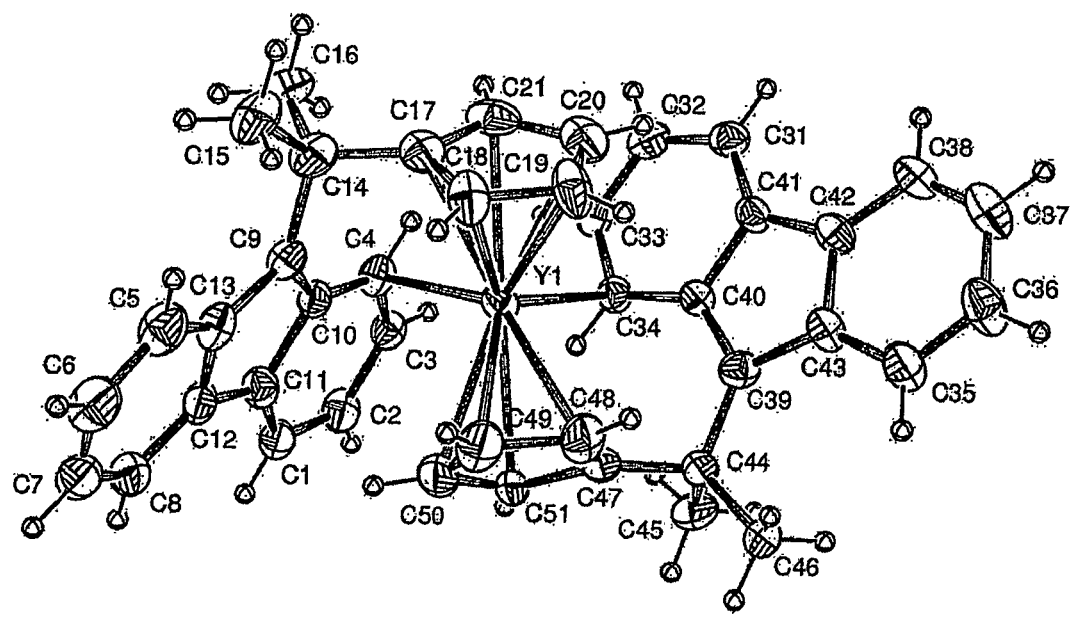
FIG. 3 represents the temperature dependence of the $^1H$ NMR spectra of the mixture obtained in step e) in THF-$d_8$ solution.

Synthesis of $(\eta^5,\eta^5\text{-Cp-CMe}_2\text{-Flu})Y(C_3H_5)(THF)$.

A "one-pot" synthesis of $(\eta^5,\eta^5\text{-Cp-CMe}_2\text{-Flu})Y(C_3H_5)(THF)$ was prepared from $YCl_3$.

To a solution of $C_{13}H_8H\text{—}CMe_2\text{—}C_5H_4H$ (1.0 g, 3.67 mmol) in diethyl ether (50 mL) at −10° C. was added under vigorous stirring 2 equiv. of n-BuLi (4.6 mL of a 1.6 M solution in hexane, 7.34 mmol). The reaction mixture was allowed to warm to room temperature. The solution turned dark-yellow and after 3 hours a yellow crystalline powder precipitated. To this suspension of the dilithium salt in ether cooled to −20° C. was added a suspension of $YCl_3(THF)_n$ (prepared from 0.72 g, 3.68 mmol of anhydrous $YCl_3$) in $Et_2O$ (50 mL). Upon vigorous stirring and warming to room temperature the reaction mixture turned deep-red. The red solution was decanted from precipitate and evaporated in vacuo to give 0.8 g of deep-red powder. To a suspension of 0.390 g of the red powder of $[(Cp\text{-}CMe_2\text{-}Flu)YCl_2]^-[Li(Et_2O)(THF)_3]^+$ in 20 mL of toluene, a solution of allylmagnesiumchloride (0.27 mL of 2M solution in THF, 0.54 mmol) was added. The reaction mixture was stirred for 8 h at room temperature. The resulting yellowish-brown solution was filtered and volatiles were removed in vacuo. The residue was washed with pentane (2×15 mL) and dried in vacuo to give a yellow powder of $(Cp\text{-}CMe_2\text{-}Flu)Y(C_3H_5)(THF)$ (0.16 g, 65%). The results of the $^1H$ NMR (toluene-$d_8$, 200 MHz, 50° C.) were as follows: δ=7.90 (d, 4H, $J_{HH}$=7.0 Hz, Flu), 7.0–6.8 (m, 4H, Flu), 5.82 (t, 1H, $J_{HH}$=2.6 Hz, Cp), 5.59 1H, $J_{HH}$=2.6 Hz, Cp), 3.13 (br m, 4H, α-$CH_2$, THF), 2.45 (br m, 2H, α-$CH_2$, THF), 2.24 (s, 6H, $CH_3$), 1.93 (br m, 4H, $CH_2CHCH_2$), 1.21 (br m, 4H, β-$CH_2$, THF). $^1H$ NMR (THF-$d_8$, 300 MHz, −70° C.): δ7.93 (d, 2H, $J_{HH}$=7.7 Hz, Flu), 7.63 (d, 2H, $J_{HH}$=7.7 Hz, Flu), 7.05 (t, 2H, Flu), 6.49 (t, 2H, Flu), 6.23 (s, 2H, Cp), 5.57 (s, 2H, Cp), 4.66 (m, 1H, $J_{HH}$=13.0 Hz, $CH_2CHCH_2$) 1.86 (s, 6H, $CH_3$), 1.52 (d, 4H, $J_{HH}$=13.0 Hz, $CH_2CHCH_2$). The results of the $^{13}C$ NMR (THF-$d_8$, 75 MHz, −70° C.) were as follows: δ=143.2 ($CH_2CHCH_2$), 132.8, 130.8, 125.6, 120.8, 120.3, 110.3, 110.1, 107.1, 106.8, 103.7, 103.5, 98.6 (Flu and Cp), 57.7 ($CH_2CHCH_2$), 38.5 ($CCH_3$).

Polymerization of Methyl Methacrylate (MMA).

To a preweighted amount of about 10 mg of $(Cp\text{-}CMe_2\text{-}Flu)Y(C_3H_5)(THF)$ in toluene, methyl methacrylate (3.0 mL, 27.7 mmol) was added by syringe and vigorous stirring at a temperature of −15° C. was immediately started. After a time period of one hour, the Schlenk tube was opened to air and acetone (30 mL) was added to quench the reaction and dissolve the polymer formed. The polymer was precipitated by adding methanol (ca. 200 mL), filtered, washed twice with methanol (30 mL) and dried in vacuo. The ratio [MMA]/[Y] was of about 300. The number average molecular weight Mn and the weight average molecular weight Mw were determined by GPC in THF using universal calibration relative to polystyrene standards. The molecular weight distribution is described by the polydispersity index D defined as the ratio Mn/Mw of the weight average molecular weight to the number average molecular weight. The polymer microstructure was determined by $^1H$ NMR in $CDCl_3$. The resulting polymer had a number average molecular weight Mn of 424,000, an polydispersity index D of 1.41 and the following tacticity: rr=67%, mr=27% and mm=6%. The yield was of 29%.

Polymerisation of Styrene.

Bulk polymerisation and solution polymedisation of styrene were carried out both with a crude sample and a recrystallised sample of $(Cp\text{-}CMe_2\text{-}Flu)Y(C_3H_5)(THF)$. The conditions and results are displayed in Table I.

TABLE I

| complex | Condit | T (° C.) | time (h) | Yield (%) | $M_n$ ($10^3$) | $M_w/M_n$ | $T_m$ (° C.) |
|---|---|---|---|---|---|---|---|
| crude | bulk | 20 | 1 | 47 | nd | nd | 269 |
| crude | toluene | 20 | 2 | 28 | nd | nd | 268 |
| recrys | bulk | 20 | 2 | 26 | nd | nd | 268 |
| recrys | toluene | 60 | 0.3 | 8 | nd | nd | |
| recrys | toluene | 60 | 0.66 | 20 | nd | nd | |

[Styrene]/[Y]~2000.

The invention claimed is:

1. A metallocene catalyst component characterized by the formula: (FluR"Cp)M($\eta^3 C_3R'_5$)(ether)$_n$ wherein Cp is a substituted or unsubstituted cyclopentadienyl group, Flu is a substituted or unsubstituted fluorenyl group, R" is a structural bridge between Cp and Flu imparting stereorigidity to the component, M is a metal of Group III of the Periodic Table, each R' is the same or different and is hydrogen, a silyl group or a hydrocarbyl group having from 1 to 20 carbon atoms and n is 0, 1 or 2.

2. The metallocene catalyst component of claim 1 wherein M is yttrium or, lanthanum.

3. The metallocene catalyst component of claim 1 wherein M is yttrium.

4. The metallocene catalyst component of claim 3 wherein R" an isopropylidene group, a diphenylmethylene group, an ethylenyl group or a dimethylsilyl group.

5. The metallocene catalyst component of claim 4 wherein R" is an isopropylidene group.

6. The metallocene catalyst component of claim 5 wherein $C_3R'_5$ is $CH_2$—CH=$CH_2$.

7. The metallocene catalyst component of claim 3 wherein said ether group is selected from the group consisting of tetrahydrofuran, dioxane, diethyl ether and diisopropyl ether.

8. The metallocene catalyst component of claim 7 wherein said ether group is tetrahydrofuran or diethyl ether.

9. A method of preparing metallocene catalyst component characterized by the formula: (FluR"Cp)M($\eta_3 C_3R'_5$)(ether)$_n$ wherein Cp is a substituted or unsubstituted cyclopentadienyl group, Flu is a substituted or unsubstituted fluorenyl group, R" is a structural bridge between Cp and Flu imparting stereorigidity to the component, M is a metal of group III of the Periodic Table, each R' is the same or different and is hydrogen, a silyl group or a hydrocarbyl group having from 1 to 20 carbon atoms and n is 0, 1 or 2, the method comprising: (a) providing a suspension of MCl$_3$(THF)$_n$ in an ether; (b) providing a suspension of a dilithium salt of (CpR"Flu) in an ether; (c) reacting suspensions (a) and (b) at molar ratio of suspension (b) to suspension (a) of less than 2 in a salt metathesis reaction at a temperature of from −80° C. to 60° C.; (d) crystallizing the product of said salt metathesis reaction from said ether in the form of a crystalline powder; (e) recovering said crystalline powder and alkylating said crystalline powder with an alkylating agent incorporating ($C_3R'_5$) in a solvent at a temperature of from −80° C. to 60° C., to produce said metallocene catalyst component; and (f) retrieving a neutral complex of said metallocene catalyst component.

10. The method of claim 9 wherein the molar ratio of suspension (b) to suspension (a) is about 1.

11. The method of claim 9 wherein said alkylating agent is selected from the group consisting of ClMg($C_3R'_5$) and Li($C_3R'_5$).

12. The method of claim 9 wherein said salt metathesis reaction is carried out at a temperature of about 20° C.

13. The method of claim 9 wherein the ether is tetrahydrofuran or diethyl ether.

14. The method of claim 9 wherein the solvent is toluene.

15. A polymerization process comprising: (a) providing a catalyst system effective for the polymerization of ethylenically unsaturated monomers which catalyst system comprises a metallocene catalyst component characterized by the formula: (FluR"Cp)M($\eta^3 C_3R'_5$)(ether)$_n$ wherein Cp is a substituted or unsubstituted cyclopentadienyl group, Flu is a substituted or unsubstituted fluorenyl group, R" is a structural bridge between Cp and Flu imparting stereorigidity to the component, M is a metal of group III of the Periodic Table, each R' is the same or different and is hydrogen, a silyl group or a hydrocarbyl group having from 1 to 20 carbon atoms and n is 0, 1 or 2; (b) contacting said catalyst system with an ethylenically unsaturated monomer in a polymerization reaction zone under polymerization conditions to form a polymer product; and (c) recovering said polymer product from said polymerization reaction zone.

16. The process of claim 15 wherein said monomer is a non-polar monomer selected from the group consisting of ethylene, a $C_3$+ alpha olefins, and styrene.

17. The process of claim 15 wherein said monomer is a polar monomer selected from the group consisting of a methacrylate and a diene.

18. The process of claim 15 wherein in said metallocene catalyst component M is yttrium or lanthanum and R" an isopropylidene group, a diphenylmethylene group, an ethylenyl group or a dimethylsilyl group.

19. The process of claim 18 wherein in said metallocene catalyst component $C_3R'_5$ is $CH_2$—CH=$CH_2$.

20. The process of claim 19 wherein in said metallocene catalyst component said ether group is selected from the group consisting of tetrahydrofuran, dioxane, diethyl ether and diisopropyl ether.

* * * * *